United States Patent
Sargeant et al.

(10) Patent No.: US 8,834,418 B2
(45) Date of Patent: Sep. 16, 2014

(54) MOLDS FOR IN SITU FORMING MATERIALS

(75) Inventors: Timothy Sargeant, Guilford, CT (US); Joshua Stopek, Guilford, CT (US); Arpan Desai, Hamden, CT (US); Atu Agawu, Princeton, NJ (US); Saumya Banerjee, Hamden, CT (US)

(73) Assignee: Covidien LP, Mansfield, MA (US)

( * ) Notice: Subject to any disclaimer, the term of this patent is extended or adjusted under 35 U.S.C. 154(b) by 268 days.

(21) Appl. No.: 13/158,728

(22) Filed: Jun. 13, 2011

(65) Prior Publication Data

US 2012/0022495 A1    Jan. 26, 2012

Related U.S. Application Data

(60) Provisional application No. 61/366,604, filed on Jul. 22, 2010.

(51) Int. Cl.
*A61M 5/00*     (2006.01)
*A61B 17/00*    (2006.01)
*A61B 19/00*    (2006.01)
*A61B 17/34*    (2006.01)

(52) U.S. Cl.
CPC . *A61B 17/00491* (2013.01); *A61B 2017/00473* (2013.01); *A61B 19/5202* (2013.01); *A61B 2017/3419* (2013.01); *A61B 2017/005* (2013.01); *A61B 2017/00495* (2013.01)
USPC ............... 604/117; 604/20; 604/21; 606/213

(58) Field of Classification Search
USPC ......... 604/20, 21, 81, 116, 117, 191; 606/213
See application file for complete search history.

(56) References Cited

U.S. PATENT DOCUMENTS

| | | | |
|---|---|---|---|
| 4,335,719 A | | 6/1982 | Johnston |
| 5,092,376 A | * | 3/1992 | Blankenship et al. ......... 141/25 |
| 5,222,939 A | | 6/1993 | Tiefenbrum et al. |
| 5,372,585 A | | 12/1994 | Tiefenbrum et al. |
| 5,437,631 A | * | 8/1995 | Janzen .......................... 604/506 |
| 5,800,373 A | | 9/1998 | Melanson et al. |
| 5,860,948 A | | 1/1999 | Buscemi |
| 6,576,000 B2 | | 6/2003 | Carrison |
| 7,037,490 B2 | | 5/2006 | Rowe et al. |
| 2004/0193043 A1 | | 9/2004 | Duchon et al. |
| 2005/0209601 A1 | | 9/2005 | Bowman et al. |
| 2006/0253082 A1 | * | 11/2006 | McIntosh et al. ............. 604/191 |
| 2008/0121657 A1 | | 5/2008 | Voegele et al. |
| 2008/0138414 A1 | | 6/2008 | Huckle et al. |
| 2008/0139694 A1 | | 6/2008 | Ratcliffe |
| 2009/0143765 A1 | | 6/2009 | Slocum et al. |
| 2009/0259180 A1 | * | 10/2009 | Choi ............................. 604/117 |
| 2009/0264810 A1 | | 10/2009 | Eppstein et al. |
| 2010/0228182 A1 | * | 9/2010 | Clark et al. ..................... 604/21 |
| 2011/0009737 A1 | * | 1/2011 | Manstein ...................... 600/424 |
| 2011/0208238 A1 | * | 8/2011 | Hoffman ....................... 606/213 |

* cited by examiner

*Primary Examiner* — Emily Schmidt

(57) ABSTRACT

An applicator for use in tissue repair is provided. The applicator includes a base configured to dispense a material and an applicator tip operably connected to the base. The applicator tip includes a body having a distal end configured to engage a tissue defect and a mold disposed about the body configured to engage tissue about the tissue defect. The mold is configured to be selectively positioned about the distal end of the body between at least a first position and a second position to deposit material to form at least a first layer and a second layer. Also provided are applicator tips, methods and kits for tissue repair.

17 Claims, 7 Drawing Sheets

MOLDS FOR IN SITU FORMING MATERIALS

CROSS-REFERENCE TO RELATED APPLICATION

The present application claims the benefit of and priority to Provisional Application Ser. No. 61/366,604, filed Jul. 22, 2010, the disclosure of which is incorporated by reference herein in its entirety.

BACKGROUND

1. Technical Field

The present disclosure relates to the repair of tissue using biocompatible fillers. More particularly, the present disclosure relates to applicators and/or applicator tips for applying the biocompatible fillers to tissue defects.

2. Background of Related Art

Materials and methods for effecting tissue repair are known. Such methods use biocompatible materials to provide stability, allow for tissue ingrowth and/or replace damaged tissue at a target site. The biocompatible material may include cells harvested from the patient, from another person and/or from another species. Additionally, or in the alternative, such materials may be synthetic. For example, commonly owned U.S. application Ser. No. 12/778,256, filed May 12, 2010, the content of which is herein incorporated by reference in its entirety, discloses methods and devices for treating osteochondral defects using biphasic plugs. For ease of application, many filler materials are applied in a liquid or viscous form, and require time and/or exposure to energy, i.e., light, to harden and/or polymerize.

Applicators for mixing and dispensing these biocompatible materials used in tissue repair are also known. Such applicators are configured to mix and/or dispense one or more materials and may be configured to discharge the material(s) as a spray or stream to a target site. The viscous consistency of the material when first dispensed from the applicator requires that the target site be horizontally positioned such that the material remains within the target site until hardened. Because the target site may be oriented in a limitless number of configurations, positioning a patient such that the target site is horizontal may be difficult, time consuming, costly and/or put the patient in a compromising position.

Therefore, it would be beneficial to have a system for tissue repair in which the target site does not need to be maintained in a horizontal positioned during the application of a material.

SUMMARY

According, an applicator for use in tissue repair is provided. The applicator includes a base configured to dispense a material and an applicator tip operably connected to the base. The applicator tip includes a body having a distal end configured to engage a tissue defect and a mold disposed about the body configured to engage tissue about the tissue defect. The mold is configured to be selectively positioned about the distal end of the body between at least a first position and a second position to deposit material to form at least a first layer and a second layer.

In some embodiments, the mold forms a seal with the tissue about the tissue defect. The base may be configured to dispense two or more materials. The mold may also, or instead, include a distal surface that is flat, concave, convex, or saddle-shaped. The distal end of the body may include a threaded surface configured to engage a threaded portion of the mold. In one embodiment, rotation of the mold relative to the base causes longitudinal translation of the mold. The base may further include at least one of a means for irrigation, a means for aspiration, a means for viewing and a means for polymerizing. The mold itself may be flat, concave, convex, saddle-shaped, flat or other shapes as well. In another embodiment, the applicator tip includes an articulation joint. The distal end of the applicator tip may be operably connected to the mold using one of a ball-and-socket joint, a flex hinge, cylindrical pivots, hinge pins and elastomeric spines.

Also provided is an applicator tip for use in tissue repair. The tip includes a body having a proximal end configured for operable connection to a means for dispensing at least a first material, a distal end configured to be received within a tissue defect and defining at least a first lumen extending therethrough. The tip further includes a mold disposed about the body and configured to engage tissue about the tissue defect. The mold is configured to be selectively positioned relative to a distal surface of the body to dispense material therefrom at a first layer and at least a second layer.

In another embodiment, the body may include at least a second lumen for providing at least one of, fluid for irrigation, suction for aspiration, a channel for viewing and/or providing a polymerizing light and a passage for providing a catalyzing material. The body may include a threaded surface configured to threadingly engage a threaded portion of the mold. In one embodiment, rotation of the mold relative to the body causes longitudinal translation of the mold relative to the distal surface of the body. In another embodiment, the mold may be moved slideably along the longitudinal axis to adjust the distance between the body and the mold.

Also provided is an applicator tip for use in the repair of tissue. The applicator tip includes a body having a mold positioned on a distal end thereof. The mold is configured to engage tissue about a tissue defect. The body is configured to deposit material at a first layer in the tissue defect. The applicator tip further includes an extension configured for selective engagement with the distal end of the body. The extension is configured to be received within the tissue defect to deposit material at a second layer in the tissue defect. In one embodiment, a proximal end of the body is configured for operable connection to an applicator base. The body may include at least a lumen for providing at least one of, fluid for irrigation, suction for aspiration, a channel for viewing and/or providing a polymerizing light and a passage for providing a catalyzing material.

Additionally provided is a kit for tissue repair. The kit includes an applicator tip having a body which includes a mold positioned on a distal end thereof. The mold is configured to engage tissue about a tissue defect. The body is configured to deposit material at a first layer in the tissue defect. The kit further includes at least one extension configured for selective engagement with the distal end of the body. The extension is configured to be received within the tissue defect to deposit material at a second layer in the tissue defect. The kit may further include a base configured to be operably connected to the applicator tip for dispensing one or more materials.

Also provided is a method of repairing tissue. The method of tissue repair includes the steps of providing an applicator configured for dispensing at least a first layer and a second layer of material, engaging tissue about a tissue defect, depositing material at the first layer within the tissue defect, adjusting the applicator to deposit material at the second layer, depositing material at the second layer and disengaging the applicator from the tissue.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIGS. 8A-8E are various extensions for use with the applicator tip of FIG. 8.

DETAILED DESCRIPTION

Figure 1:
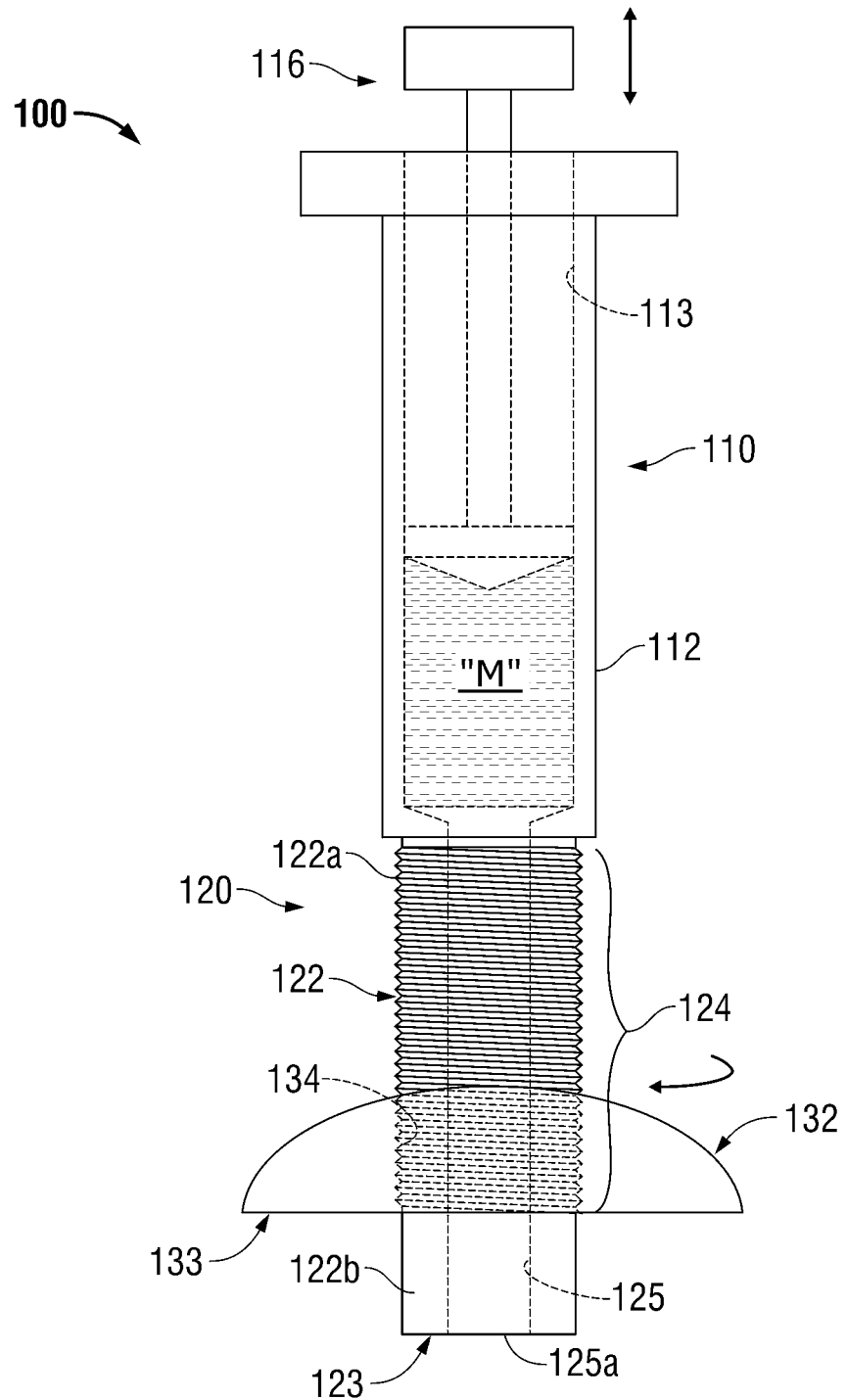
FIG. 1 is a side view of an applicator according to an embodiment of the present disclosure.

Embodiments of the presently disclosed system for repairing tissue defects will now be described in detail with reference to the drawings wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the instrument which is further away from the user.

Figure 2:
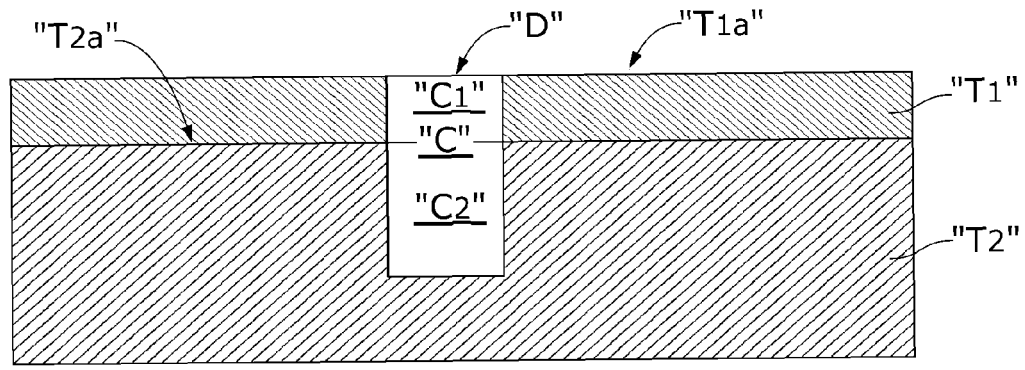
FIG. 2 is a cross-sectional side view of a tissue defect in tissue having first and second layers.

Referring initially to FIG. 1, an assembly for dispensing a biocompatible material is shown generally as applicator 100. Applicator 100 includes an applicator base 110 and an applicator tip 120. Applicator 100 is configured to dispense a biocompatible material from within base 110 through applicator tip 120 and into a tissue defect "D" (FIG. 2). Although the embodiments of the present disclosure will be described as relates to cartilage repair, it is envisioned that the embodiments may be modified for use in repairing other tissue, e.g., bone defects, muscle defects, fistulas, ulcers, and other soft tissue defects.

Still referring to FIG. 1, briefly, applicator base 110 includes a substantially cylindrical body 112 defining a cavity 113 for receiving a biocompatible material. Applicator base 110 further includes a plunger 116 configured to operably engage cylindrical member 112 to cause the ejection of a biocompatible material "M" from cavity 113. As shown, applicator base 110 is configured for dispensing a single, premixed biocompatible material. The rate at which the biocompatible material is dispensed is determined by the rate at which plunger 116 is depressed. Applicator base 110 may be provided to a clinician preloaded, or instead, may be filled by the clinician prior to use.

As will be discussed in further detail below, embodiments of the presently disclosed applicator tip may be modified to include mixing assemblies, e.g., blades and rotors; polymerizing assemblies, e.g., UV-light source, and/or irrigation/aspiration assemblies, e.g., compressible member or plunger. Alternatively, the applicator tip may be configured for use with an applicator base including any or all of these various designs and capabilities. For example, applicator tip 120 may be modified for use with an applicator base (not shown) capable of mixing one or more multi-component materials and/or dispensing more than one biocompatible material. The applicator base may also, or instead, include irrigation and/or aspiration functions.

With reference still to FIG. 1, applicator tip 120 is operably connected to applicator base 110. Applicator tip 120 may be integrally formed with base 110, as shown, or instead may be selectively or fixedly attached thereto using adhesive, threading, bayonet coupling or other suitable means. Applicator tip 120 includes a substantially cylindrical body 122 and a selectively movable mold 132 operably positioned thereon. Either or both of body 122 and mold 132 may be formed of plastic, polymer, or other suitable material. Either or both of body 122 and mold 132 may be flexible, semi-flexible, or rigid and/or may be transparent or translucent. As shown, applicator tip 120 includes a single lumen 125 in fluid communication with cavity 113 of applicator base 110. Lumen 125 is configured for dispensing biocompatible material "M" within tissue defect "D". As discussed above, applicator tip 120 may be modified for use with various applicator bases including those capable of dispensing more than one biocompatible material. Accordingly, applicator tip 120 may be modified to include one or more lumens and each of the lumens may be used for more than one function. In one embodiment, and as shown, lumen 125 includes a valve 125a in a distal end thereof to prevent backflow of biocompatible material therethrough.

With reference to FIGS. 1-5, a proximal end 122a of body 122 includes a threaded outer surface 124 configured for receiving mold 132 in a longitudinally adjustable manner. The adjustability of mold 132 relative to body 122 may be modified by varying the size and/or pitch of the threads. In alternative embodiments, mold 132 may be longitudinally adjustable along body 122 using other mechanical or electrical means including, with a notch and groove configuration, using adjustable fasteners and/or through fiction fit. Body 122 may include markings (not shown) for determining the depth of a distal surface 123 of body 122 relative to a distal surface 133 of mold 132. Body 122 includes a distal end 122b configured to be received within an opening or defect "D" in a first layer of tissue, i.e., cartilage. Distal surface 123 of body 122 is configured to lay flush with an outer surface "$T_{2a}$" of a second layer of tissue "$T_2$", i.e., bone, adjacent a cavity "$C_2$" created in second layer of tissue "$T_2$". Typically, a cavity "C" formed in first and second layers of tissue "$T_1$, $T_2$" is created by a drill or other boring instrument while removing damaged or defective tissue and creating space to receive the biocompatible material. As will be discussed in further detail below, during use, the positioning of distal surface 123 flush with the outer surface of second layer of tissue "$T_2$" seals cavity "$C_2$" within second layer of tissue "$T_2$". Because cavity "$C_2$" created in second layer of tissue "T$_2$" is sealed, a patient, and more particularly the body part of the patient that includes the tissue repair site, need not be oriented in a horizontal position to retain initially viscous biocompatible material "M" within cavity "C$_2$". Instead, the sealed cavity "C$_2$" created by applicator tip 120 maintains material "M" with cavity "C$_2$" regardless of the orientation of cavity "C$_2$". Distal surface 123 of body 122 may be flat, as shown, or may instead be concave, convex or include any other suitable configuration to facilitate a better seal with outer layer "T1$_a$" of first layer of tissue "T$_1$". Furthermore, distal surface 123 of body 122 may be smooth, as shown, or instead may include a textured configuration. The textured configuration may assist/prevent adhesion of biocompatible material "M" to tissue and/or other materials, may promote/prevent tissue in-growth, may act to strengthen/weaken hardened or semi-hardened biocompatible material "M", and/or for any other suitable purpose.

Referring still to FIGS. 1-5, mold 132 includes a threaded inner surface 134 configured to engage threaded exterior surface 124 of body 122 Inner surface 134 may be threaded along an entire length thereof, or instead, may only be partially threaded, as shown. Either or both of body 122 and mold 132 may include a stop mechanism (not shown) for preventing over-translation of mold 132 relative to body 122. Either or both of body 122 and mold 132 may further include a securing mechanism (not shown), i.e., set pin, for selectively preventing movement of mold 132 and body 122 relative to each other.

Figure 1A:
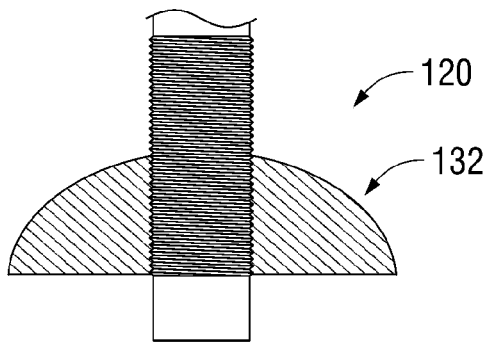
FIGS. 1A-1C are molds for use with the applicator of FIG. 1, having various configuration including convex (FIG. 1A), concave (FIG. 1B) and saddle-shaped (FIG. 1C)
Figure 1B:
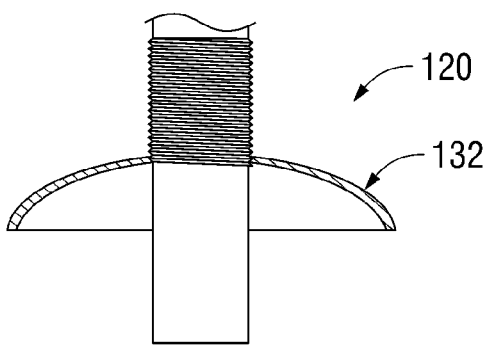
Figure 1C:
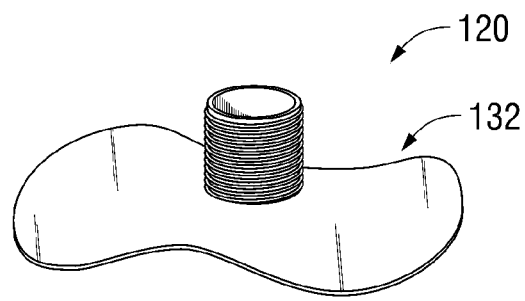

As shown in FIG. 1, distal surface 133 of mold 132 is substantially flat. Alternatively, distal surface 133 of mold 132 may be substantially convex (FIG. 1A), substantially concave (FIG. 1B), saddle-shaped (FIG. 1C) or otherwise configured to conform to outer surface "T$_{1a}$" of a first layer of tissue "T$_1$" (FIG. 2). Distal surface 133 of mold 132 may be smooth, as shown, or instead may include a textured configuration. As with distal surface 123 described above, a textured configuration may assist/prevent adhesion of the biocompatible material to tissue and/or other materials, may promote/prevent tissue in-growth, may act to strengthen/weaken the hardened biocompatible material, and/or for any other suitable purpose. Mold 132 is constructed of polymer, plastic or other suitable material. Mold 132 may be flexible or include a flexible distal surface 133. The flexible nature of mold 132 permits mold 132 to conform to outer surface "T$_{1a}$" of a first layer of tissue "T$_1$", thereby increasing the integrity of the seal created with the tissue.

With reference to FIGS. 1-5, the use of applicator 100 will now be described in repairing a defect including multiple layers of tissue. Although shown including two layers of tissue "T$_1$", "T$_2$", applicator 100 may be used in the repair of defects in only a single layer of tissue and in the repair of defects extending through multiple layers of tissue. Prior to use of applicator 100, a tissue defect is identified and its dimensions established. Depending on the type of defect and its location, damaged tissue is typically removed using a drill or other boring instrument. Removal of the damaged tissue in this manner creates a uniform opening or cavity "C" in the tissue in which to deposit biocompatible material "M". Cavity "C" includes a first portion, cavity "C$_1$" defined by first tissue layer "T$_1$" and a second portion, cavity "C$_2$" defined by second tissue layer "T$_2$".

Figure 3:
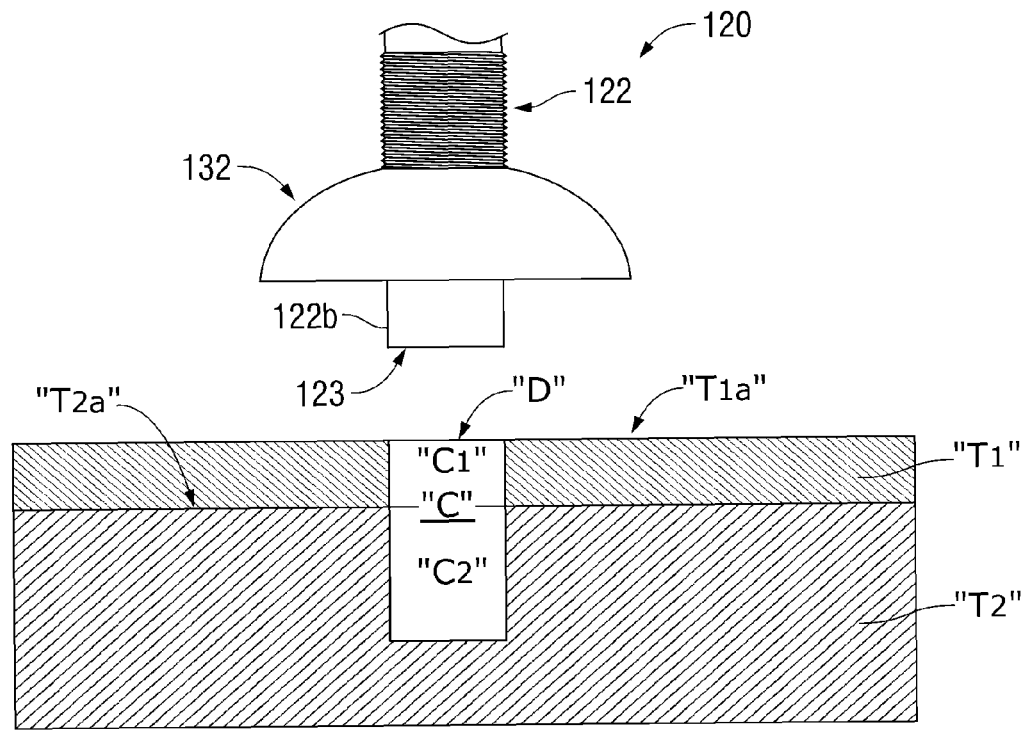
FIG. 3 is a partial cross-sectional side view of the tissue defect of FIG. 2 and the applicator tip of the applicator of FIG. 1.
Figure 4:
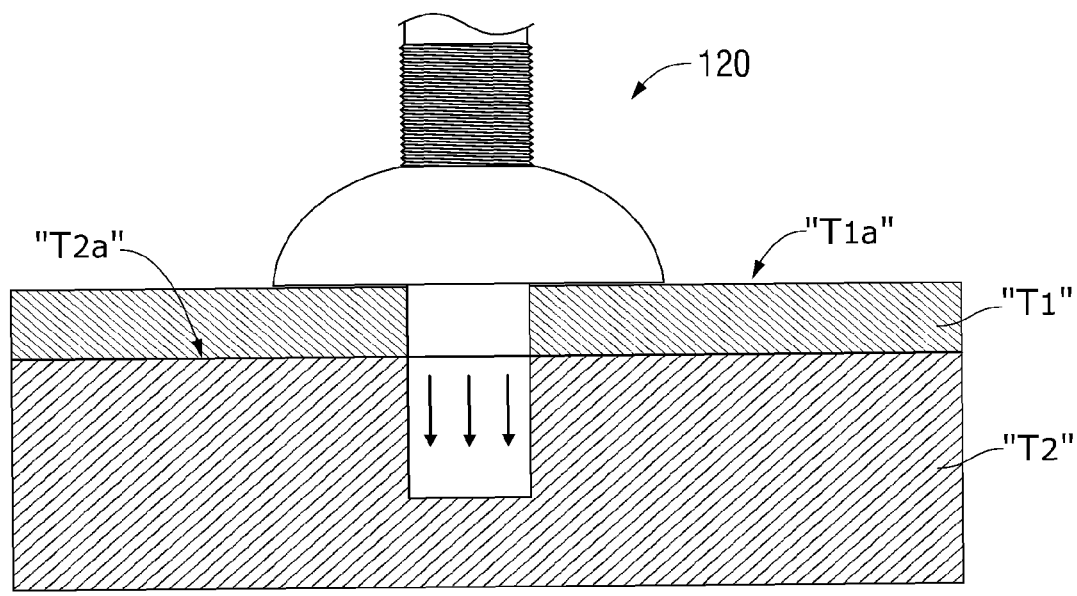
FIG. 4 is a partial cross-sectional side view of the tissue defect and applicator tip of FIG. 3, with a distal end of the applicator tip in a first configuration engaging the tissue defect.

With particular reference now to FIGS. 2 and 3, once a defect has been identified and the damaged tissue has been removed, the diameter of the defect and the thickness of first layer of tissue "T$_1$" are determined. An appropriate applicator tip 120 may then be selected and is adjusted to accommodate the defect. In this embodiment, applicator tip 120 is adjusted by rotating mold 133 about body 122 to longitudinally translate mold 132 relative to distal surface 123 of body 122. Mold 132 is adjusted such that distal surface 123 of body 122 is received flush with proximal surface "T$_{2a}$" of second tissue layer "T$_2$" when distal end 122$a$ of body 122 is received within cavity "C$_1$" and distal surface 133 of mold 132 engages proximal surface "T$_{1a}$" of first tissue layer "T$_1$". In this manner, distal surface 123 of body 122 operates to seal cavity "C$_2$" formed by second tissue layer "T$_2$".

Once distal surface 123 of body 122 is properly positioned relative to proximal surface "T$_{2a}$" of second tissue layer "T$_2$", plunger 116 is depressed to cause the ejection of biocompatible material "M$_1$" from applicator 100 and into cavity "C$_2$". The sealed nature of cavity "C$_2$" permits the filling of cavity "C$_2$" with the initially viscous first biocompatible material "M$_1$" regardless of the orientation of cavity "C$_2$", i.e., at orientations other than horizontal. Applicator tip 120 is configured to remain in place during the polymerization and/or hardening of first biocompatible material "M$_1$". As discussed above, applicator 100 may be provided to a clinician pre-loaded with a first biocompatible material "M$_1$", or instead, may require loading by the clinician. As also discussed above, applicator 100 may include a light source (not shown) or other polymerizing mechanism to assist in the hardening of first biocompatible material "M$_1$".

Once first biocompatible material "M$_1$" has hardened sufficiently, distal end 122$b$ of body 122 is retracted proximally relative to distal surface 133 of mold 132 until distal surface 123 of body 122 is flush with distal surface 133 of mold 132. This may be accomplished by rotating body 122 relative to mold 132 while maintaining distal surface 133 of mold 132 in engagement with proximal surface "T$_{1a}$" of first layer of tissue "T$_1$". Alternatively, applicator tip 120 is removed from engagement with tissue "T$_1$" thereby allowing for rotation of mold 133 relative to body 122. Once distal surface 133 of mold 132 and distal surface 123 of body 122 are aligned, distal surface 133 of mold 133 is positioned adjacent proximal surface "T$_{1a}$" of first layer of tissue "T$_1$" such that distal surface 123 of body 122 is aligned with and adjacent to defect "D". In this manner, distal surface 123 of body 122 seals cavity "C$_1$".

Figure 5:
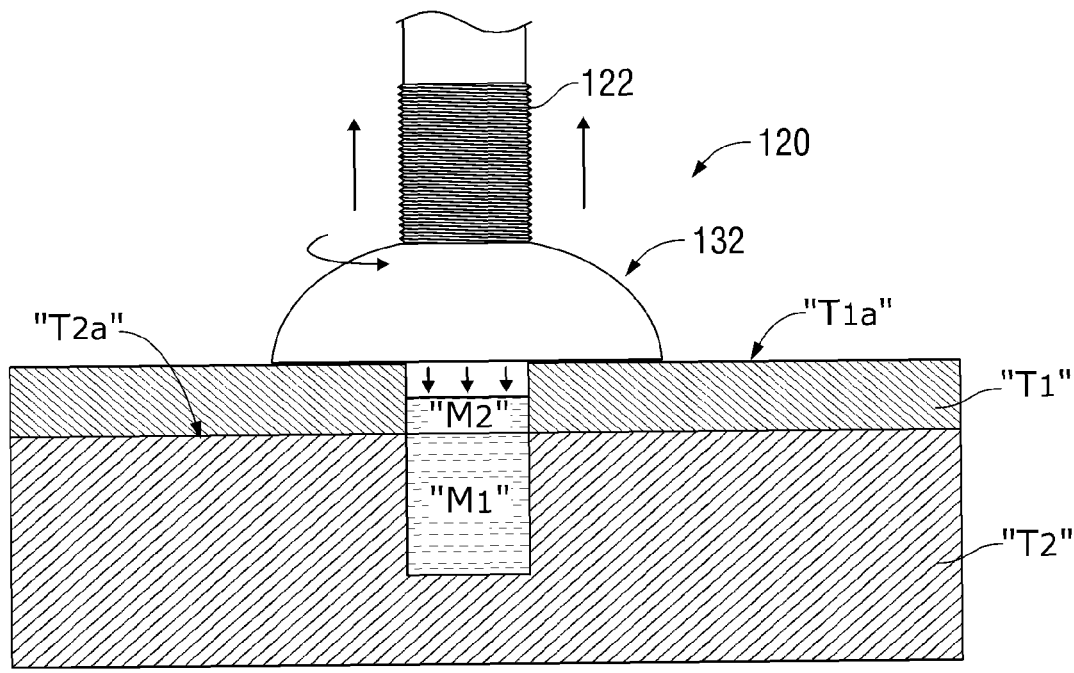
FIG. 5 is a partial cross-sectional side view of the tissue defect and applicator tip of FIGS. 3 and 4, with a distal end of the applicator tip in a second configuration engaging the tissue defect.

With reference now to FIG. 5, once applicator tip 120 has been repositioned with respect to cavity "C", a second biocompatible material "M$_2$" is dispensed from applicator 110. As shown, applicator base 110 is configured for dispensing a single biocompatible material "M$_1$" from a single cavity 113, therefore, plunger 116 must be removed and a second biocompatible material "M$_2$" added to cavity 113 of applicator base 110. As discussed above, applicator base 110 may be selectively removable from applicator tip 120. In this manner, applicator base 110 previously including first biocompatible material "M$_1$" is removed and is replaced by a second applicator base (not shown) including a second biocompatible material. As also discussed above, applicator base 110 may instead include an alternative configuration including more than one cavity for maintaining biocompatible materials "M". As discussed above with regards to cavity "C$_2$", the sealed nature of cavity "C$_1$" permits the filling of cavity "C$_1$" with an initially viscous second biocompatible material "M$_2$" regardless of the orientation of cavity "C$_1$", i.e., at orientations other than horizontal. Applicator tip 120 is configured to remain in place during the polymerization and/or hardening of second biocompatible material "M$_2$". As discussed above, applicator 100 may include a polymerizing mechanism to facilitate hardening of the biocompatible material. Once second biocompatible material "M₂" has hardened and/or polymerized, applicator tip 120 is removed from engagement with first tissue "T₁".

Figure 6:
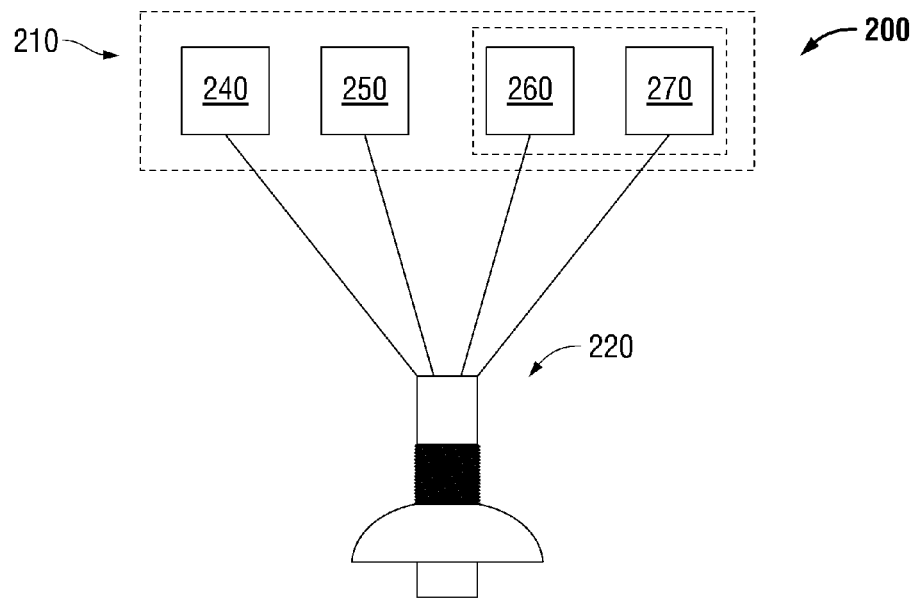
FIG. 6 is a schematic view of an applicator system according to an alternative embodiment of the present disclosure.

Turning now to FIG. 6, an embodiment of a tissue repair system according to the present disclosure is shown generally as tissue repair system 200. Tissue repair system 200 includes an applicator base 210 and an applicator tip 220. Applicator tip 220 is substantially similar to applicator tip 120 described hereinabove, including a body 222 and a selectively adjustable mold 232. Applicator base 210 includes first and second sources of biocompatible material 240, 250 and may optionally include a source of irrigation fluid 260 and/or a means for aspiration 270. Either or both of first and second sources of biocompatible material 240, 250 may be integrally formed with applicator tip 220. Alternatively, either or both of first and second sources of biocompatible materials 240, 250 may be remotely located relative to applicator tip 220. In this manner, tissue repair system 200 is adaptable for use in repairing tissue in less accessible locations. Either or both of first and second sources of biocompatible material 240, 250 may be configured to mix and dispense respective first and second biocompatible materials (not shown). Either or both of irrigation and aspiration sources 260, 270 may be integrally formed with applicator tip 220. Alternatively, either or both of irrigation and aspiration sources 260, 270 may be remotely located relative to applicator tip 220, thus, reducing the size of applicator base 210. Although shown including first and second sources of biocompatible material 240, 250, it is envisioned that tissue repair system 200 may be configured to include only a single source or multiple sources of material.

Figure 7A:
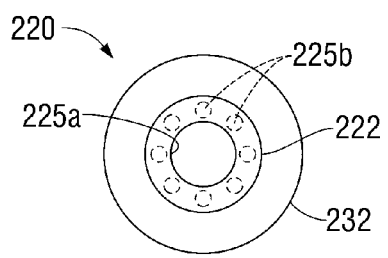
FIGS. 7A-7C are end views of various embodiments of an applicator tip including a central lumen with a plurality of lumens thereabout (FIG. 7A), a plurality of concentric lumens (FIG. 7B) and various sized and positioned lumens (FIG. 7C)
Figure 7B:
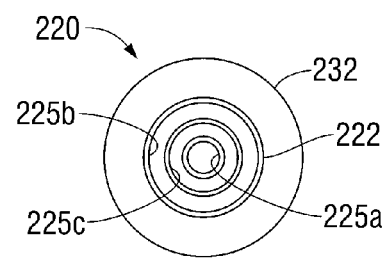
Figure 7C:
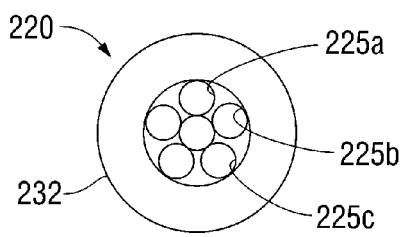

Applicator tip 220 may include a single lumen extending therethrough configured for dispensing the biocompatible material as well as providing passage for irrigation and/or aspiration. Alternatively, and with reference to FIGS. 7A-7C, applicator tip 220 includes a plurality of lumen 225a, 225b, 225c. As shown in FIG. 7A, applicator tip 220 may include a large central lumen 225a and a plurality of smaller lumen 225b radially disposed thereabout. Instead, as shown in FIG. 7B, applicator tip 220 includes a first central lumen 225a, and one or more concentric lumens 225b, 225c, or as shown in FIG. 7C, applicator tip 220 includes a plurality of various sized lumens 225a, 225b, 225c. Any or all of lumen 225a, 225b, 225c may be configured for fluid communication with any of first and second source of biocompatible material 240, 250, irrigation source 260 and means for aspiration 270 to provide the respective functions. Any one of the lumens may be configured to provide a catalyzing or polymerizing effect, including by delivering high/low pH salts/solutions and copper for click chemistry and providing a channel for a fiber optic capable of directing UV or other polymerizing light. For example, the applicators and methods of the current application may be used with hydrogel compositions that include compositions that react with each other upon contact as well as precursors that react upon contact with an initiator such as those disclosed in commonly owned U.S. application Ser. No. 13/115,017, filed May 24, 2011, the content of which is herein incorporated by reference in its entirety. Any one of the lumens may further be configured to receive a camera or other viewing device. Additionally, any one of the lumens may be configured to receive a sensing device capable of sensing the level or amount of material deposited within cavity "C" (FIG. 2). Alternatively, a sensing mechanism (not shown) may be incorporated into a distal end of body 222.

Figure 8:
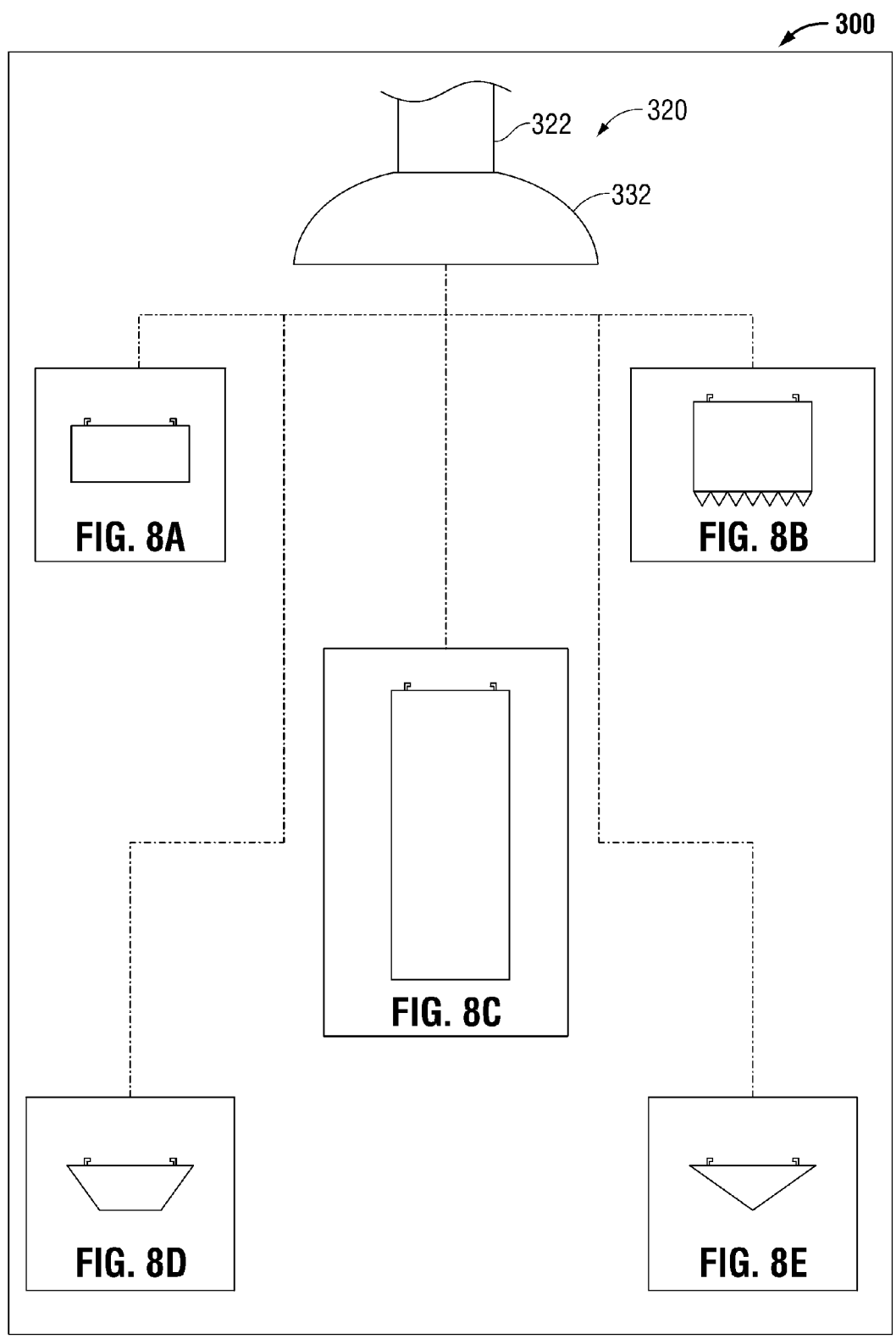
FIG. 8 is a top view of a kit including an applicator tip according to another embodiment of the present disclosure and various extensions.

Turning now to FIGS. 8-8E, the applicator tip of an alternate embodiment of an applicator according to the present disclosure is shown generally as applicator tip 320. Applicator tip 320 includes a base 322 and mold 332 rigidly secured to base 322. Applicator tip 320 further includes a variety of extensions configured to selectively engage mold 332. The extensions may be of various sizes and dimensions configured to be received within defects of various sizes and dimensions. For example, the extension may include a small cylindrical body (FIG. 8A), a large cylindrical body having a textured distal surface (FIG. 8B), an elongated cylindrical body (FIG. 8C), a frustroconical body (FIG. 8D), a triangular body (FIG. 8E) or other suitable configuration. The extensions of the various configurations or of one configuration in various sizes may be provided as a kit 500. Kit 300 may further include applicator tip 320. In an alternative embodiment, kit 300 may include an applicator base (not shown) configured to selectively engage applicator tip 320. In another embodiment, kit 300 includes an applicator (not shown) including applicator tip 320 integrally formed or securely attached thereto.

Figure 9:
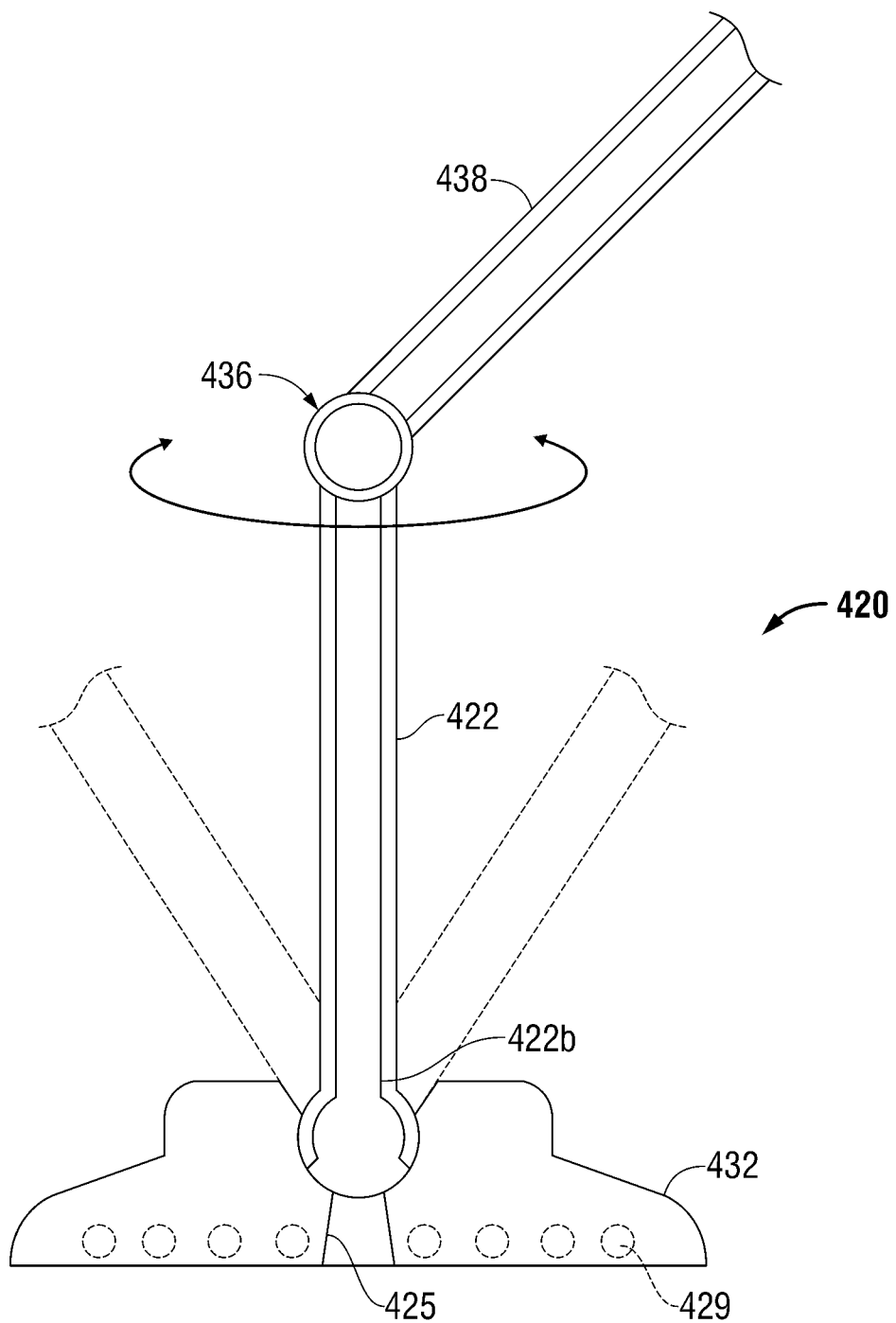
FIG. 9 is a side view of an applicator tip according to yet another embodiment of the present disclosure.

Referring now to FIG. 9, another embodiment of an applicator tip according to the present disclosure is shown generally as applicator tip 420. Applicator tip 420 includes a body 422 adjustably positioned relative to a mold 432. As shown, body 422 is pivotally secured to mold 432 at a distal end 422b thereof in a ball-and-socket configuration. In this manner, body 422 may be rotated three-hundred and sixty degrees (360°), relative to mold 432, as shown by arrow "A". In alternative embodiments, body 422 may be connected to mold 432 with a flex hinge (not shown), hinge pins (not shown), cylindrical pivots (not shown) or elastomeric spines (not shown). Further, applicator tip 420 includes at least one articulation joint 436 to provide for additional manipulation of applicator tip 420. A second articulation joint (not shown) would permit applicator body 422 to be further manipulated, i.e., in a goose-neck manner. Applicator tip 420 also includes a source of polymerizing light 429 (shown in phantom) integrally formed therewith for assisting in the polymerization of material that has been dispensed therethrough. Alternatively, the source of polymerizing light is included in the applicator base, or remotely, and applicator body 422 is configured to direct the light to the distal surface thereof.

Although the illustrative embodiments of the present disclosure have been described herein with reference to the accompanying drawings, it is to be understood that the disclosure is not limited to these precise embodiments, and that various other changes and modifications may be effected therein by one skilled in the art without departing from the scope or spirit of the disclosure. For example, a polymerizing light and or articulation joint may be incorporated into any of the presently disclosed applicator tips.

What is claimed is:

1. An applicator for use in repairing a tissue defect, the applicator comprising:
 a base configured to dispense at least first and second materials; and
 an applicator tip operably connected to the base, the applicator tip including:
  a body defining a longitudinal axis and having a distal end configured to engage a tissue defect; and
  a mold disposed about the body configured to engage tissue about the tissue defect, wherein the mold is configured to be selectively positionable relative to the distal end of the body between at least a first position along the longitudinal axis to deposit the first material to form a first layer and a second position along the longitudinal axis to deposit the second material to form a second layer, wherein the distal end of the body includes a flat distal surface configured to lay flush with a distal surface of the mold when the mold is in one of the first and second positions.

2. The applicator of claim 1, wherein the mold forms a seal with tissue about a tissue defect.

3. The applicator of claim 1, wherein the base is configured to dispense more than two materials.

4. The applicator of claim 1, wherein the mold includes a distal surface that is flat, concave, convex, or saddle shaped.

5. The applicator of claim 1, wherein the distal end of the body includes a threaded surface configured to engage a threaded portion of the mold.

6. The applicator of claim 5, wherein rotation of the mold relative to the base causes longitudinal translation of the mold.

7. The applicator of claim 1, wherein the base further includes at least one of a means for irrigation, a means for aspiration, a means for viewing, or a means for polymerizing.

8. The applicator of claim 1, wherein the mold is at least one of flat, concave, convex, or saddle shaped.

9. The applicator of claim 1, wherein the applicator tip includes an articulation joint.

10. The applicator of claim 1, wherein the distal end of the applicator tip is operably connected to the mold using one of a ball-and-socket joint, a flex hinge, cylindrical pivots, hinge pins and elastomeric spines.

11. The applicator of claim 1, wherein the mold and the body are coaxial.

12. The applicator of claim 1, wherein the body defines at least one concentric lumen formed about a central lumen.

13. An applicator tip for use in repairing a tissue defect, the tip comprising:

a body defining a longitudinal axis and including a proximal end configured for operable connection to a means for dispensing first and second filler materials and a distal end configured to be received within a tissue defect and defining at least a first lumen extending therethrough, wherein the distal end includes a distal surface extending perpendicular to the longitudinal axis; and a mold disposed about the body and including a saddle shape configured to engage tissue about a tissue defect, wherein the mold is configured to be selectively positioned along the longitudinal axis relative to the distal surface of the body between at least a first position wherein the first filler material dispensed from the distal end of the body forms a first layer and the second filler material dispensed from the distal end of the body forms a second layer.

14. The applicator tip of claim 13, wherein the body includes at least a second lumen for providing at least one of: fluid for irrigation, suction for aspiration, a channel for viewing and/or providing a polymerizing light, and a passage for providing a catalyzing material.

15. The applicator tip of claim 13, wherein the body includes a threaded surface configured to threadingly engage a threaded portion of the mold.

16. The applicator tip of claim 15, wherein rotation of the mold relative to the body causes longitudinal translation of the mold relative to the distal surface of the body.

17. The applicator tip of claim 13, wherein the mold and the body are coaxial.

* * * * *